(12) United States Patent
Bluecher et al.

(10) Patent No.: US 10,953,138 B2
(45) Date of Patent: Mar. 23, 2021

(54) DEVICE WITH MICROSTRUCTURE MEDIATED ABSORPTION PROFILE

(71) Applicant: BVW Holding AG, Cham (CH)

(72) Inventors: Lukas Bluecher, Eurasburg (DE); Kenneth Kleinhenz, Santee, CA (US); Michael Milbocker, Holliston, MA (US)

(73) Assignee: BVW HOLDING AG, Cham (CH)

( * ) Notice: Subject to any disclaimer, the term of this patent is extended or adjusted under 35 U.S.C. 154(b) by 226 days.

(21) Appl. No.: 16/164,444

(22) Filed: Oct. 18, 2018

(65) Prior Publication Data

US 2019/0117849 A1    Apr. 25, 2019

Related U.S. Application Data

(60) Provisional application No. 62/574,180, filed on Oct. 18, 2017, provisional application No. 62/620,831, filed on Jan. 23, 2018.

(51) Int. Cl.

| | |
|---|---|
| *A61L 27/58* | (2006.01) |
| *A61L 27/18* | (2006.01) |
| *A61L 31/06* | (2006.01) |
| *A61L 27/34* | (2006.01) |
| *A61L 31/10* | (2006.01) |
| *A61L 27/22* | (2006.01) |
| *A61L 31/14* | (2006.01) |

(Continued)

(52) U.S. Cl.
CPC ............... *A61L 27/58* (2013.01); *A61L 27/18* (2013.01); *A61L 27/22* (2013.01); *A61L 27/34* (2013.01); *A61L 31/06* (2013.01); *A61L 31/10* (2013.01); *A61L 31/148* (2013.01); *A61L 27/30* (2013.01); *A61L 31/043* (2013.01)

(58) Field of Classification Search
CPC .......... A61B 17/00; A61F 2002/30062; A61L 27/58; A61L 2/18; A61L 31/06
See application file for complete search history.

(56) References Cited

U.S. PATENT DOCUMENTS

| | | | |
|---|---|---|---|
| 2007/0198040 A1* | 8/2007 | Buevich | A61L 31/146 606/151 |
| 2008/0109072 A1* | 5/2008 | Girton | A61L 31/16 623/1.49 |

(Continued)

FOREIGN PATENT DOCUMENTS

| | | |
|---|---|---|
| WO | 2009129631 | 10/2009 |
| WO | 2011127395 | 10/2011 |

*Primary Examiner* — Jason-Dennis N Stewart
(74) *Attorney, Agent, or Firm* — Patterson Intellectual Property Law, P.C.; Ryan D. Levy; Mark A. Kilgore

(57) ABSTRACT

Polymer devices are disclosed with microstructured surfaces that modify their absorption pathway. Polymers which generally degrade in water by fracturing into high surface energy fragments, are modified to degrade in vivo without the formation of sharp fragments. Devices are disclosed that possess improved handling characteristics and degrade in an aqueous environment in a uniform and continuous way that favors the formation of soluble monomers rather than solid particulate. Absorbable medical implants with the disclosed surface modifications are more biocompatible, with reduced foreign body response, and dissolution into metabolizable molecular species.

19 Claims, 5 Drawing Sheets

(51) Int. Cl.
  *A61L 27/30* (2006.01)
  *A61L 31/04* (2006.01)

(56) References Cited

U.S. PATENT DOCUMENTS

2014/0343667 A1* 11/2014 McClain ............... A61L 31/126
                                                  623/1.38
2017/0014111 A1   1/2017 Hulseman et al.

* cited by examiner

DEVICE WITH MICROSTRUCTURE MEDIATED ABSORPTION PROFILE

CROSS-REFERENCE TO RELATED APPLICATIONS

This application claims the benefit of priority to U.S. provisional application No. 62/574,180, filed on Oct. 18, 2017, and U.S. provisional application No. 62/620,831, filed on Jan. 23, 2018, each of which is hereby incorporated by reference in its entirety.

TECHNICAL FIELD

The present invention relates, in general, to surface textured absorbable devices, and in particular to devices used in the field of surgery and, more particularly, to surgical implants made of absorbable polymer.

BACKGROUND

While this section is largely devoted to established observations and theories, some of the material contained in this section is new with respect to interpretation or perceived application, nevertheless the underlying theory is known. Thus, the applicants do not intend that ideas disclosed in this section necessarily constitute prior art, and that some of the connections made between variant states of prior art may constitute invention, especially with regards to the mechanism of promoting surface hydration of microstructured devices.

Fluid pinning is an important way to localize water on specific regions of a solid substrate. Wetting is the relationship between a liquid phase and a solid phase, and wetting is essential to fluid pinning. Wetting is characterized by a contact angle at the interface between a liquid and a solid surface. The contact angle is representative of the intermolecular interactions between the liquid and solid wherein the energy of interaction is minimized. The contact angle can also be associated with a force balance between adhesive and cohesive forces. Wetting is important in the bonding or adherence of two materials.

There are two types of wetting: non-reactive (static) wetting and active (dynamic) wetting. Adhesive force between a liquid and solid cause a liquid drop to spread across the surface of the solid (Wenzel wetting). Cohesive force within the liquid causes the drop to ball up and avoid contact with the surface (Cassie-Baxter wetting). The juxtaposition of the adhesive and cohesive forces results in fluid pinning, which is essentially a balance between the tendency for a fluid to spread adherently on a surface and the tendency for a fluid to resist attachment and spreading on a surface.

The contact angle is a complicated function of surface texture and chemical composition of the relevant phases. When the contact angle is small for a liquid on a surface texture, the liquid-solid interface is said to be in a Wenzel state. When the contact angle is large for a liquid on a surface texture the liquid-solid interface is said to be in a Cassie-Baxter state. When part of a liquid is in a Wenzel state and another part of the liquid is in a Cassie-Baxter state, the combined state is said to be in a Wenzel-Cassie state.

When two solid surfaces form a liquid interface, such as between an implant and a body, surface texture plays a large role in the hydration of the implant surface. A scale of interaction between a microstructured surface and a living surface is defined by the surface texture of the microstructured device. The microstructure is typically hierarchical, and characterized by at least two spatial scales, one on the order of 1-10 micrometers (microns) and another on the order of 10-1000 microns.

It should be appreciated, that in this disclosure, hierarchical means microstructures of different spatial scale. A hierarchical microstructure is defined on a two-dimensional surface characterized by dimensions x and y, and out-of-plane dimension z. Each microstructure scale can be defined by characteristic dimensions x', y' and z' residing on a two-dimensional surface described by function f(x, y). Function f(x, y) is not necessarily planar. A hierarchical microstructure is a set of scaled microstructures, each characterized by (x', y', z'), (x", y", z"), and so on; wherein, a first microstructure resides in a region defined by (x, y, z1) and a second microstructure resides in a region defined by (x, y, z2), and so on. The range z1 spans a range of z values defined by zmin<z1<zmax, and so on. A hierarchical microstructure is a three-dimensional microstructure where most of the first microstructure resides in region z1, and most of the second microstructure resides in region z2, and so on, such that z1>z2> . . . with respect to an arbitrary set of Euclidean coordinates (x, y, z). For example, a hierarchical microstructure may comprise a set of cylinders of height 10 and diameter 2 arranged on the top surfaces of cylinders arranged in a plane of height 100 and diameter 20.

A hierarchical microstructure is self-similar if the ratio of feature dimensions scale by a constant factor. The self-similarity may occur in all of the scale dimensions, or any subset of the scale dimensions. In the example of cylinders, the pitch between cylinders at various spatial scales p1, p2, p3, . . . is self-similar, if the pitches satisfy the constant ratios p1/p2=p2/p3= . . . =c, where c is a constant. Pitch is defined as the distance between the centers of two like-structures. In most cases the pitch is constant for a given type of structure. Aspect ratio is a related measure, which is defined as the ratio of the height of a structure to its width.

Now referring to the composition of implantable materials, bioresorbable polymers, such as aliphatic polyester polymers derived from lactic acid and glycolic acid are used clinically as sutures, bone fracture fixation devices and sustained drug delivery systems. The mechanism of their degradation in aqueous media is a matter of discussion in the literature.

PLA/GA polymers are a class of stereo copolymers and copolymers that degrade heterogeneously in situ. The degradation in the bulk of the polymer is faster than at the surface where a layer of less degraded material forms. This has been observed in vitro and in vivo.

In the particular case of intrinsically amorphous PLA/GA materials the phenomenon is particularly significant since polymer degradation leads to hollow structures when the inner oligomeric residues become soluble and leach out. These hollow structures subsequently fracture, leaving a multiplicity of sharp, high surface energy fragments that then initiate a chronic inflammatory response. This late-time initiation of inflammation, at a time when the initial insult of the implantation is residing, is responsible for delayed healing and chronic inflammation leading to necrosis.

Generally speaking, polymeric skin formation after immersion in an aqueous medium is initiated with water uptake. The penetrating water rapidly creates a negative gradient of water concentration from the surface to the bulk center line. Degradation then begins from the inside.

Hydrolysis is the most common form of polymer degradation. Soluble oligomers are formed and readily escape from the bulk polymer. Soluble oligomers close to the surface leach out before total degradation, whereas those located well inside the bulk remain entrapped and contribute significantly to an autocatalytic effect. The resulting difference in concentration of acidic groups results in the formation of a skin composed of degradation resistant polymer.

The thickness of the skin depends on many factors such as the diffusion rates of various evolved species and the rate of bond cleavage. Diffusion coefficients of the soluble oligomers depend primarily on molar mass, degree of polymer swelling in the bulk, and macromolecular conformation and rigidity. Degradation rates can depend on the sequential distribution of chiral and achiral units along the polymer chains. The release of soluble oligomers depends on surface energy, including pH-mediated boundary layers, ionic strength and buffering. If the degrading polymer is or becomes crystalline, bulk degradation can proceed faster that amorphous forms of similar composition.

Paradoxically, the applicants expect implants with thickness less than twice the critical skin thickness to degrade more slowly and more uniformly. The unexpected effect is due to the leachable oligomeric compounds escaping before significant auto-catalysis of bulk hydrolysis or enzymatic degradation can take place.

There is anecdotal evidence to support the hypothesis that the greater the thickness of an implant the faster the degradation. Grizzi et al found that large scale devices made of PLA50 degraded faster than smaller devices, in good agreement with a diffusion-catalysis model.

The terms "degradable", "bioresorbable" and "absorbable" in the present context are used interchangeably, and apply to polymers that disintegrate by a number of processes, including physical disintegration, biodegradation by biological mechanisms, and chemical reaction to monomer units. Materials that undergo only physical disintegration have limited utility as implants, since they typically elicit prolonged foreign body response. Ideally, the monomers resulting from polymer degradation are metabolized by the biological systems into which they are implanted.

One approach to preventing polymer skin formation is to modify the surface properties of the polymer. Surface property modification can be achieved by irradiation, e.g. with laser light, ion and electron beams, UV light, X- and g-rays or treatment in plasma discharge. Irradiation leads to degradation of polymeric chains, chemical bond cleavage, creation of free radicals and release of gaseous degradation products. One disadvantage of surface modification by irradiation is the release of transient, highly reactive species. Other undesirable effects are formation of excessive double bonds, production of low mass stable degradation products, large crosslinked structures and oxidized structures.

Another approach to surface modification involves exposure to plasma discharge. The degree of modification and character of induced changes depend on the composition of ambient atmosphere, energy of plasma ions, temperature during the treatment and discharge power. Surface properties of a polymer can be changed continuously, such as wettability, adhesion, chemical resistance, lubrication or biocompatibility.

Plasma treatment is disadvantageous in several respects. The surface modification is typically only tens of micrometers thick. The modified surface properties are quickly reversed in an aqueous environment, making plasma treatment ineffective in implant situations. Plasma treatment is an extremely complex process requiring precise control of plasma composition, flow and pressure of the gas, substrate temperature, reactor geometry, discharge power and frequency.

These observations suggest intentional surface texture design may mitigate against polymer skin formation. Surface texture engineering is a known way to permanently modify the surface energy of a polymer. Precise design of the texture on a polymer surface can inhibit fragmented degradation morphologies. In particular, in the manufacture of biocompatible implants, the applicants found matching the surface texture to the polymer skin thickness is an important enabling consideration.

The relationship between polymer surface microstructure and biosorption kinetics plays a significant role in biocompatibility metrics. Surface microstructure can act as degradation nucleation sites that determines implant fractionation and dissolution. Implant degradation that involves sharp, high surface energy particulate formation can trigger a variety of cellular responses which can adversely affect the biocompatibility of the implant. In particular, chronic inflammatory response has been associated with implant degradation morphology associated with sharp, solid phase degradation products.

Polymer systems with homogeneous microstructure display simultaneous polymer degradation and monomer release. The surface texture of a polymer can affect biosorption rates and the shape of the released degradation products. For heterogeneous copolymers, the risk of high surface energy particulate formation is the greatest. Surface texturing can confuse the degradation process, and mediate against degradation along boundaries between heterogeneous regions.

The applicants have discovered that the cellular response mechanism to an implant can be directed by polymer surface microstructure, enhancing the biocompatibility of the implant.

The degree to which an implant acts as a tissue scaffold and not a foreign body source of irritation plays a pivotal role in an implant's biocompatibility. Whenever cell seeding, proliferation, and new tissue formation can be promoted, the degree of reaction oxygen species release is diminished. The most biocompatible implants are those that degrade at a rate comparable to the rate of new tissue formation. Surface texture modification can be used to match degradation rates to cellular infiltration rates.

New tissue formation is inhibited by the presence of reactive oxygen species and cellular infiltrates associated with inflammation. A few surface modification techniques such as salt leaching, fibrous fabric processing, gas foaming, emulsion freeze-drying, three-dimensional printing, and phase separation have been used to enhance cellular infiltration on implants. However, typically these approaches ignore the degradation kinetics of the polymeric material comprising the implant. Furthermore, the highly porous nature of many polymer scaffolds for tissue engineering promote particulate formation, that ultimately interferes with healthy tissue recruitment. These scaffolds have shown great promise in the research of engineering a variety of tissues. However, to engineer clinically useful tissues and organs is still a challenge. The understanding of the principles of polymer surface texture and degradation morphology is far from satisfactory.

Surface feature size, connectivity between feature domains, and surface area are widely recognized as important parameters for a scaffold for tissue engineering. Other architectural features such as feature shape, hierarchical morphology, and spatial periodicity between features of the scaffolding materials are also believed to be important for cell seeding, migration, growth, mass transport, gene expression, and new tissue formation in three dimensions.

BRIEF SUMMARY

The present invention concerns implants with surface microstructure capable of 1) minimizing migration of an implant inside a body, 2) promoting healthy tissue infiltration and the avoidance of foreign body response, 3) exceptional flexibility compared to an implant of the same material and thickness without surface microstructure, 4) directing the range of sizes of adverse particulate formation in the case a foreign body response occurs, and most importantly 5) promoting surface hydration and inhibiting bulk polymer hydration. The last feature promotes dissolution of the implant into soluble monomers and inhibits the formation of solid phase particulate, in particular the surface texture inhibits formation of particulate with high surface energy.

The present invention is an environmentally absorbable device designed to degrade without the formation of particulate. In particular, a surgical implant made of a polymer that degrades while implanted in the tissue of a patient, and the surgical implant has a preferential hydration zone adapted to degrade at a different rate than the rest of the surgical implant. For the embodiments described herein, the surgical implant is illustrated as a surgical soft tissue reinforcement device that may be formed into a sheet when deployed into tissue, although the present invention also is applicable to many other kinds of implants, prostheses, and other polymeric surgical implants. The present invention is not limited to medical applications, and may be particularly useful in the manufacture of plastic articles with enhanced environmental degradation rates.

The applicants have fabricated implantable polymer surfaces with bioabsorption-directing surface textures to create degradation pathways with enhanced biocompatibility. Using well-controlled inter-feature connectivity, the biodegradable polymer devices of the present invention control the rate and particulate size of degradation products.

In one embodiment, the preferential hydration zone comprises hierarchical surface microstructures that provides high surface area for surface-specific hydration.

In another embodiment, the surgical implant has a stacked hierarchical surface over at least a portion of its surface, and the preferential hydration zone comprises a self-similar zone of surface texture.

In another embodiment, the surgical implant develops the preferential hydration zone during deployment of the surgical implant into the tissue of the patient. In one version of this embodiment, the preferential hydration zone comprises a microstructure that undergoes hydrolysis or enzymatic degradation preferentially during deployment of the surgical implant, thereby causing dissolution of at least a portion of the polymer of the surgical implant to the tissue of the patient.

In a further embodiment, the surgical implant is a surgical soft tissue reinforcement device that is deployable in physical contact and acting as a surgical barrier against adhesion formation between tissue layers of the patient. In this embodiment the surface microstructure serves to localize the implant against migration, and to prevent particulate degradation of the implant. The applicants have found that a hierarchical surface microstructure can improve the handling properties of the implant. For example, surface microstructure reduces the likelihood of implant folds that often result from trying to fit a flat implant to a curving tissue surface. The surface microstructure significantly enhances the precision of suture placement, and reduces the force required to pierce the implant.

In one version of this embodiment, the microstructure provides a migration resistant means whereby the surface texture adheres to the patient tissue.

In another version of this embodiment the surface texture alters the surface energy of the polymer, and in particular is hydrophilic to promote hydration of a first surface of the device. The first surface hydrolytically dissolves at an interface between the device and the patient tissue and does not form solid phase particulate.

An object of the present invention is the manufacture of an absorbable medical implant having a biocompatible, absorbable core portion and a bioabsorbable textured outer surface portion overlying the core portion.

An object of the present invention is a textured implant useful as a prosthesis for tissue augmentation, adhesion barrier, or drug delivery.

An object of the present invention is a biocompatible implant with a textured outer surface portion enveloping the core portion and presents a high surface area, bioabsorbable textured surface to the exterior environment. As a capsule forms around the implant following implantation, the irregular contour of the outer surface of the implant causes the surface of the implant to hydrate to a greater degree than the bulk material thus preventing polymer skin formation which inhibits fractional disintegration of the implant either during the formation of the capsule and/or after the capsule is formed. The outer bioabsorbable surface portion of the implant is absorbed by the body of the host by reduction of the molecular weight of the polymeric constituents of the implant, reducing them to soluble, lower molecular weight moieties, and not to solid phase particulate.

An object of the present invention is to provide a flexible soft tissue augmentation implant comprised of polylactic acid, polylactic acid/polyglycolic acid copolymer or polyester urethane with surface microstructure capable of 1) minimizing migration of an implant inside a body, 2) promoting healthy tissue infiltration and the avoidance of foreign body response, 3) exceptional flexibility compared to an implant of the same material and thickness without surface microstructure, 4) directing the range of sizes of adverse particulate formation in the case a foreign body response occurs, and most importantly 5) promoting surface hydration and inhibiting bulk polymer hydration.

The features of the invention believed to be novel are set forth with particularity in the appended claims. However the invention itself, both as to organization and method of operation, together with further objects and advantages thereof, may be best understood by reference to the following description taken in conjunction with the accompanying drawings in which:

DESCRIPTION OF THE PREFERRED EMBODIMENTS

Figure 1:
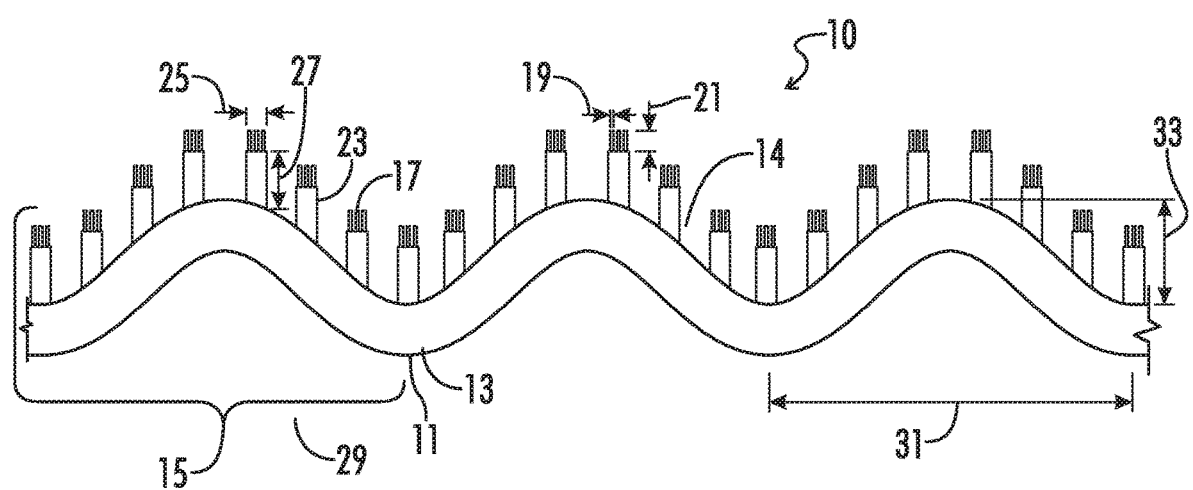
FIG. 1 is a cross-sectional view of a portion of a first preferred embodiment of an implant in accordance with the present invention.

With reference to FIG. 1, a medical implant in accordance with the present invention is shown in cross-sectional view at numeral 10. The implant 10 comprises a (normally extensible) polylactic acid core 11. The elastomeric core 11 has an inner bulk 13 and an outer surface 14. The outer surface 14 of the core 11 is characterized by a plurality of microstructures 15 disposed on the surface portion of the core 11. The microstructures 15 are dimensioned to permit the passage of fibroblasts thereinto. The microstructures 15, in accordance with textured outer surfaces 14 are of three types, the first type 17 preferably dimensioned in the range of 1-15 microns in diameter 19 and 10-25 microns in height 21. The second type 23 preferably dimensioned in the range of 25-50 microns in diameter 25 and 26-50 microns in height 27. The third type 29 preferably dimensioned in the range of 100-500 microns in diameter 31 and 100-500 microns in height 33. The arrangement of the microstructures is important because tissue ingrowth requires the migration of fibroblast cells into the pores to facilitate deposition of connective tissue between the microstructures. Such connective tissue, deposited between the microstructures, is integral with and part of the structure of the implant. It is believed that the irregular topography of the outer surface 14 of the implant induces non-inflammatory healing in the adjacent tissue layers comprising the surrounding body.

Figure 2:
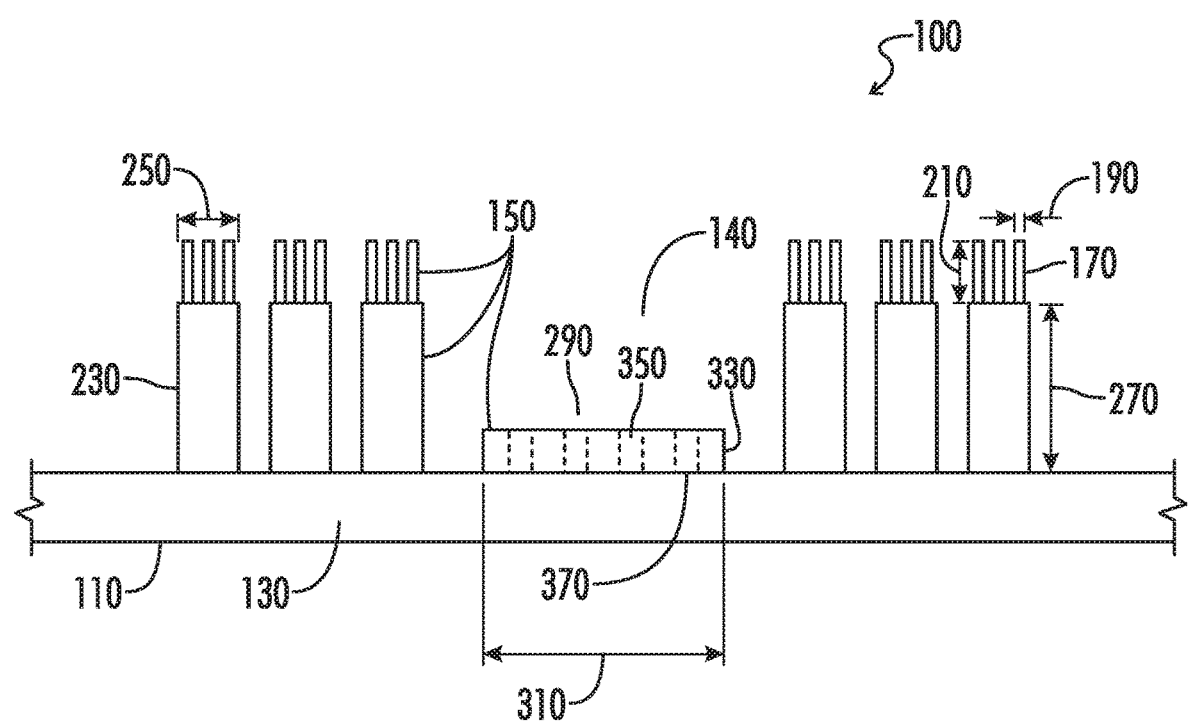
FIG. 2 is a cross-sectional view of a portion of a second preferred embodiment of an implant in accordance with the present invention.

With reference to FIG. 2, a medical implant in accordance with the present invention is shown in cross-sectional view of a portion of a second preferred embodiment of an implant in accordance with the present invention at numeral 100. The implant 100 comprises a (normally extensible) polylactic acid core 110. The elastomeric core 110 has an inner bulk 130 and an outer surface 140. The outer surface 140 of the core 110 is characterized by a plurality of microstructures 150 disposed on the surface portion of the core 110. The microstructures 150 are dimensioned to permit the passage of endothelial cells thereinto. The microstructures 150, in accordance with textured outer surfaces 140 are of three types, the first type 170 preferably dimensioned in the range of 1-15 microns in diameter 190 and 10-25 microns in height 210. The second type 230 preferably dimensioned in the range of 25-50 microns in diameter 250 and 26-50 microns in height 270. The third type 290 preferably dimensioned in the range of 100-500 microns in diameter 310 and 10-50 microns in height 330. Drilled into feature 290 are holes 350 of depth equaling height 330 and diameter 10-50 microns 370.

Figure 3:
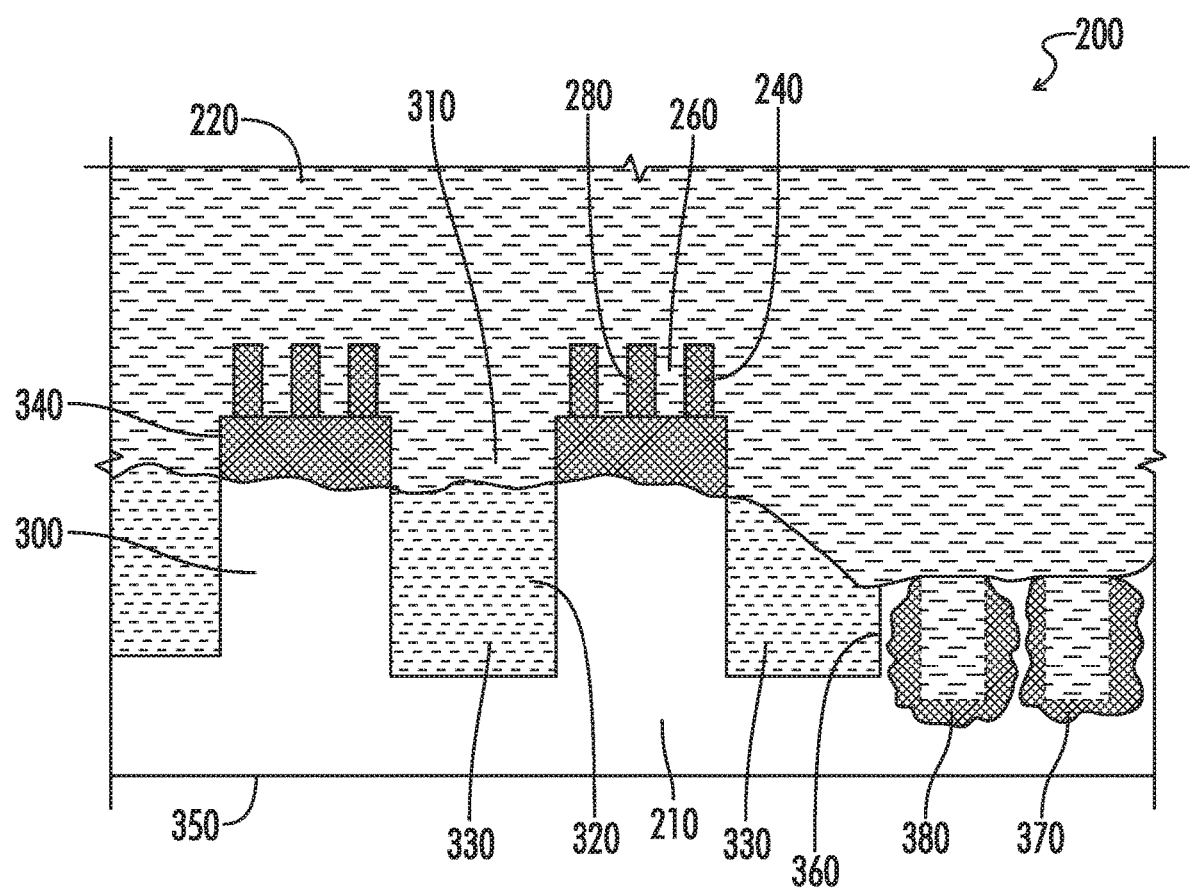
FIG. 3 is a cross-sectional view of the second preferred embodiment of an implant in accordance with FIG. 2, and following implantation within the body, showing the hydration of the microstructure thereon.

With respect to FIG. 3, a medical implant in accordance with the present invention is shown in cross-sectional view of the second preferred embodiment of an implant in accordance with FIG. 2, and following implantation within the body, showing the hydration of the microstructure thereon 200. The implant 210 is immersed in an aqueous environment 220. Fine microstructure 240 is hydrophilic and water completely fills channels 260. The full volume of microstructure 240 is hydrated 280. Microstructure 300 is hydrophobic and water 310 partially fills channels 320. The rest of the channel volume 320 is filled with lipid 330. Only the tips 340 of microstructure 300 are hydrated. Surface 350 is resting against tissue, or is coated and hydrates more slowly. Alternatively, the microstructures could be disposed on both sides of the implant. Microstructure 360 is made hydrophilic by the inclusion of drilled holes or channels 370. The inner surfaces 380 are partially hydrated.

Figure 4:
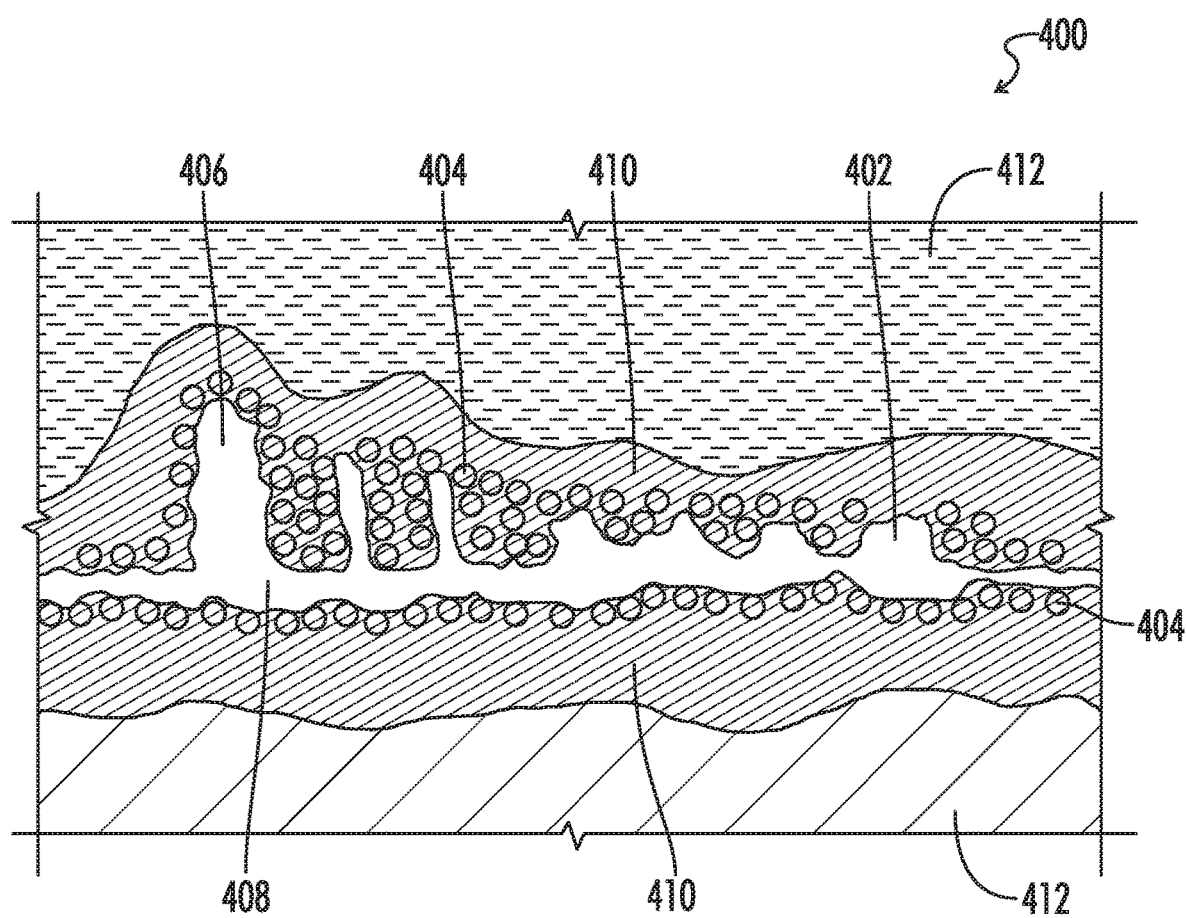
FIG. 4 is a cross-sectional view of the second preferred embodiment of an implant in accordance with FIG. 3, and following implantation within the body, showing the solvation without particulate formation of the microstructure surface thereon.

With respect to FIG. 4, a medical implant in accordance with the present invention is shown in cross-sectional view of the second preferred embodiment of an implant in accordance with FIG. 3, and following implantation within the body, showing the solvation 400 without particulate formation of the microstructure surface 402 thereon. The implant 402 is entirely encapsulated with healthy, non-fibrogenic tissue 404. Remnants of microstructure 406 have the same thickness as the core 408 of the implant 402. This state is by design, with the entire implant 402 going into dissolution at approximately the same time without particulate formation. The implant 402 is protected from particulate formation by reinforcement from encapsulating tissue 404 and uniform solvation of the absorbable polymer. Typically, the solvated monomers 410 exist as a diffuse soft cloud of monomers, which are metabolized by the surrounding tissue. Beyond the monomers 410 is water or tissue 412.

Figure 5:
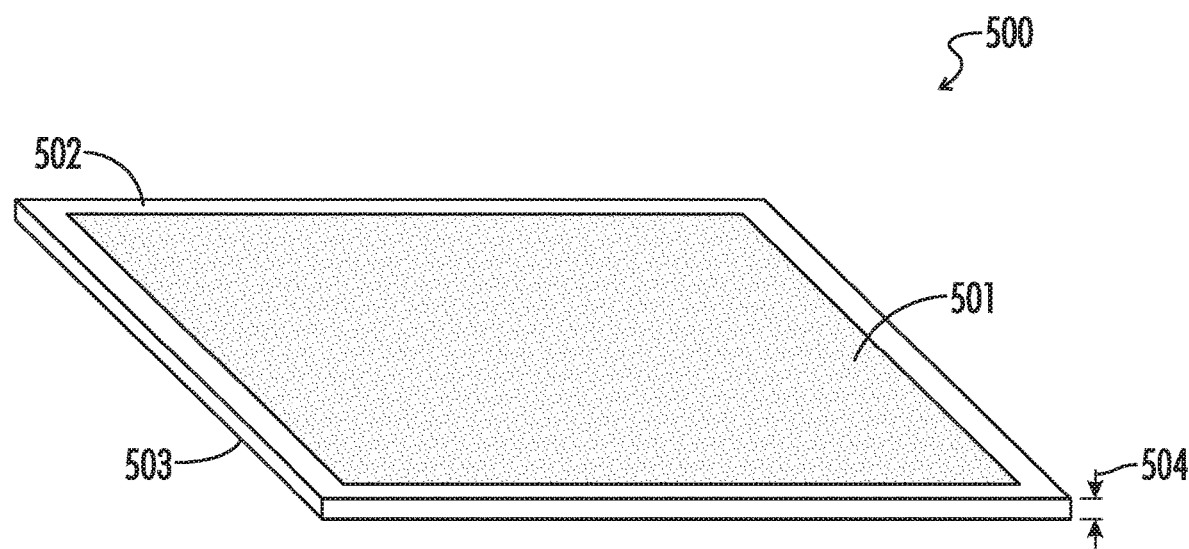
FIG. 5 depicts an implantable sheet device comprising a microstructured surface as disclosed herein.

FIG. 5 depicts an implantable sheet 500 having a microstructured surface 501 on at least a portion thereon. In some embodiments, the microstructured surface covers the entire surface of the device, while in others the microstructured surface comprises a portion of the device. Microstructured surface 501 may comprise a preferential hydration zone, as described herein below. The device has a first side 502 and a second side 503. In some embodiments, the first side comprises the microstructured surface while the second side is smooth. In other embodiments, the first and second sides each have a microstructured surface, where the surface have either the same or different morphology. The sheet has a core with a thickness 504. In certain embodiments, the sheet comprises a polyester polyurethane, particularly a polyester polyurethane as described and exemplified herein.

In the embodiments of a microstructured implant in accordance with the present invention, the choice of biodegradable material must be such that the structural integrity of the bioabsorbable portion of the implant is retained for 2-3 months following implantation in order to allow sufficient time for the implant to dissolve from the surface and avoid particulate disintegration.

The implant surface is preferably completely hydrated at the time of implantation. This encompasses the inner and outer surfaces of the microstructures. The hydration can be achieved through textures that create a Wenzel-Cassie interface with tissue. The Wenzel-Cassie interface binds water to the implant surface. The hydration preferably comprises at least one water monolayer. A multiplicity of monolayers can also be layered on top of one another utilizing a stacked hierarchical surface texture. Water molecules are bound to the surface texture through dipole-dipole bonds and/or through van der Waals forces and/or through hydrogen bridges and thus can form extended water molecule layers.

The use of an implant according to the present invention is foreseen for regulating an adsorption of proteins on the surface of the implant in terms of type, quantity and/or conformation of certain proteins by means of a defined surface, which is at least for the most part hydrated. The defined state can also have a defined surface charge and/or a defined predetermined composition of an oxide layer of the surface. The defined state is determined according to a desired regulation of the protein adsorption. Hence for different requirements for protein adsorption differing defined conditions can be established which are each attained by a suitable surface pattern. Suitable surface patterns develop in different location different surface energies, corresponding to separate locations of hydrophilicity and hydrophobicity. These alternating patterns of surface energy can promote certain types of protein adhesion, and subsequent tissue ingrowth.

Through an implant according to the present invention the quantity of proteins and other elements adhering on the surface during an implantation of the implant can be changed. For example, undesired proteins can be reduced and desired proteins settled in an increased way. More neutrophils can be settled on the implant surface, which release cathelicidin and thus are responsible for a reduction of restenosis. The adsorption of thrombocytes can be decreased. Thus the risk of complications with implantation of an implant is significantly reduced and the growing-together behavior of the implant is improved. Complications from breaking or chipping of coatings on the implant, as is known from the state of the art, are excluded.

Good results have been obtained with implants according to the invention in which the second surface microstructure is more hydrophobic than the first surface microstructure wherein the contact angle of the first microstructure is at least 10% less than the contact angle of the second microstructure, preferably by 20% or more.

Alternatively, the zeta potential value of the surface in the second microstructure should be below the zeta potential value of the first microstructure. The zeta potential can serve to determine a defined state for the implant surface. The said potential values relate to a determination procedure by means of electrokinetic analysis. With the use of other determination procedures, the indications for potential values may possibly have to be adapted according to the procedural standards.

In addition to using differences in hierarchical texture to achieve surface energy differences at discrete locations on the implant surface in order to create water pinning states, e.g., Wenzel-Cassie, such surface energy "textures" can promote healthy cellular ingrowth. Ingrowth prevents device mobilization. Implant motion can cause an inflammatory response resulting in the release of reactive oxygen species, which then cause rapid degradation of the implant and undesirable implant fragmentation.

Protein deposition on an implant is highly sensitive to surface energy, and can also affect the shape or conformation of adsorbed proteins. The conformation of proteins adsorbed on an implant surface has an influence on the adhesion of neutrophils and fibroblasts and thus on the growing-together behavior of an implant and the surrounding tissue. Proteins are complex copolymers, whose three-dimensional structure is composed of several levels. Involved in the structural composition can be amino acid sequences, different .alpha.-helix and .beta.-sheet structures, the common structure of a multiplicity of polypeptides and the like.

Natural conformation is desired, natural conformation is the shape proteins take when there are no outside influences affecting the three-dimensional structure of the proteins and influence the activity of these proteins. To be designated as an almost natural, or respectively natural-like conformation should be a conformation in which slight changes in the protein structure exist, but these changes have no influence or a negligible influence on the function and effect of the protein. Proteins comprise different regions, e.g. positively or negatively charged regions, hydrophilic and hydrophobic regions, which, depending upon spatial organization of the proteins, are exposed and can carry out specific biological functions. Through adsorption on a surface the protein conformation changes. Generally a protein has e.g. on a hydrophobic surface a greatly denatured conformation, while there exists on the hydrophilic surface a less denatured conformation. Protein conformation, because it coats the implant, can affect hydration and degradation profiles.

The hydrophilic components of the proteins in the natural conformation usually lie outside and the hydrophobic components usually lie inside and are accessible for the hydrophobic surface only through a major conformational change. Information about the protein conformation can be gained through a measurement of the behavior of .alpha.-helix and .beta.-sheets or through a measurement of specific amino acids on the protein surface.

With the present invention it was surprisingly discovered that e.g. endothelial cells can be settled on an implant surface according to the invention when fibrinogen is deposited at least approximately in its natural, or respectively natural-like, conformation. Endothelial cell infiltration promotes angiogenesis and healthy tissue association with the implant.

The efficacy of fibrinogen on an implant surface according to the invention can be improved, since fibrinogen is adsorbed primarily in an advantageous conformation. In contrast thereto, fibrinogen on an implant surface in the unhydrated state is adsorbed in a denatured state, whereby a negative influence on the growing together of an implant results. In a denatured state fibrinogen has a changed three-dimensional structure and a changed spatial distribution of different fibrinogen regions not found in the natural state. A natural conformation also with other proteins promotes a positive growing together of the implant.

The applicants have observed that a natural growing together of tissue promotes dissolution rather than fragmentation of the implant. During the implantation in a body, the body's own defense or resistance can recognize the difference between natural and denatured protein, in particular of fibrinogen, so that denatured protein is identified as a foreign body and an adverse reaction is triggered. Foreign body response results in the release of enzymes and reactive oxygen species that degrade the implant in a disordered and fragmentary manner.

In use, the amount of adsorbed proteins on the implant can vary in the defined second state of the surface compared with the starting state of the implant surface. For example, the absolute amount of adsorbed proteins can be decreased and/or certain kinds of proteins can be adsorbed in an increased way and other kinds of proteins adsorbed in a decreased way. Thus the risk can be reduced of undesired deposits of proteins. The type of adhering proteins can thus be regulated in that a suitable defined second state is generated with the hydration and for example different oxides in the oxide layer or different surface charge. Through the production of an implant with a hydrated surface the adsorption of the proteins can be influenced. Less macroglobulin and/or apolipoprotein A can adhere on the surface and more apolipoprotein E, kininogen and/or plasminogen can be adsorbed. Above and beyond this, the conformation of proteins on the surface can be regulated. For example, fibrinogen can be settled on the implant surface in a way corresponding to its natural conformation, as explained above. Its natural effectiveness is thereby preserved and the deposit of endothelial cells promoted.

Surface Texture Considerations

A critical consideration in achieving the objectives of the present invention is to match the volume, areas, depth of penetration of hydration with the dimensions of the implant. In particular, in regions of the implant where a large volume to surface area ratio exists, microstructures should be disposed on the boundary surfaces to inhibit hydration of the bulk polymer in the region of high volume to surface area. This is achieved by a Wenzel-Cassie surface texture which traps water at a distance separate from surfaces boundary to large volumes.

Other strategies include surface patterns of spatial periodic frequency suitable for encouraging protein deposition and cellular infiltration which can act as an insulating covering and reinforcement against implant fractionation into particulate. If this strategy is to be pursued, it is important that such cellular interaction not cause an inflammatory response, which could result in rapid uncontrolled enzymatic degradation of the implant, especially if such foreign body response is localized to particular regions of the implant.

Other considerations include the manner in which the microstructural elements are laid down on the device. In the print construction of an implant, there are two principal modes: a droplet configuration and a line configuration. Drops are discrete in three dimensions, whereas lines are discrete in two dimensions. Lines generally draw water by capillary action, whereas spherical drops tend to resist water.

In the droplet mode the drops can be spaced apart on a surface, and they can be joined together by a subsequent layer of drops in staggered form, or joined together by a line. The drops can be spaced closer together to slightly touch, creating an undulating profile, or they can be placed in close proximity so that they effectively merge before solidifying. In the creation of islands, they can be stacked in pyramid fashion in a vertical direction.

In the line mode the lines are generally laid down in alignment with the previous line. However draping configurations can be achieved. For example, a partial wall can be formed of several aligned lines on top of which a line is placed such that it crosses this partial wall in undulatory fashion, such that adhesion between the wall and the line is only at points. After solidification, these draping feature typically are free to move away from the established wall structure. Draping features can be placed at points intermediate during the formation of a complete wall. In addition, a partial wall can be fenestrated by subsequent layers of droplets built up to form the edges of windows, the top edge of which is closed by the subsequent addition of lines. These lines typically will droop down into the established fenestrations. By varying the deposit speed of the final lines one can create a multiplicity of drooping lines into the fenestration of different lengths creating a curtain of drooping lines.

Alternatively the microstructural elements can be deposited on a plane with a mold pattern. For example, the mold pattern can be a superhydrophobic pattern capable of generating a Wenzel-Cassie effect or a Wenzel-Baxter effect.

Other surface textures can be achieved by incorporating on or in deposited microstructural element a variety of solid particulate. The solid particulate may be a permanent nanostructure, such as a nanotubule, a bucky ball, or any of variously known nanoparticulate geometries. The solid particulate may be soluble, such that when the patterned implant is placed in a solvent the particulate are partially or entirely removed without affecting the remaining portion of the implant.

In addition, directed and random writing techniques can be combined. For example, at various points during the construction of a directed structure a spray or electrospinning technique could be employed to deposit randomly oriented fibrous or particulate masses.

Selection of Polymers

There are many materials that may be used to form a bioabsorbable implant. For example, the implant may comprise a bioabsorbable material selected from the group comprising polymers or copolymers of lactide, glycolide, caprolactone, polydioxanone, trimethylene carbonate, poly orthoesters, polyethylene oxide and polyester polyurethane. In addition to the foregoing bioabsorbable, non-toxic materials, high molecular weight polysaccharides from connective tissue such as chondroitin salts may be employed for the purpose of practicing the invention. Other polysaccharides may also prove suitable, such as chitin and chitosan. Additional bioabsorbable materials are in intense development and it is expected that many of the new materials will also be applicable for forming a textured bioabsorbable medical implant.

The manufacturing method of the patterned absorbable implant can rely on the polymer constituents being in a liquid phase. The liquid phase is typically realized by dissolution of a solid polymer in a solvent or by melting. In the case of a melt phase, it is preferable to select polymers having relatively low melting points, to avoid exposing resorbable polymers to elevated temperatures. Resorbable polymers are typically susceptible to thermal degradation.

A number of polymers are commonly used in the construction of implantable medical devices. Unless otherwise specified, the term "polymer" will be used to include any of the materials used to form the patterned implant matrix, including polymers and monomers which can be polymerized or adhered at point of application to form an integral unit.

In a preferred embodiment the microstructural elements are formed of a polymer, such as a synthetic thermoplastic polymer, for example, ethylene vinyl acetate, polyanhydrides, polyorthoesters, polymers of lactic acid and glycolic acid and other a hydroxy acids, and polyphosphazenes, a protein polymer, for example, albumin or collagen, or a polysaccharide containing sugar units such as lactose.

In a more preferred embodiment the polymers are absorbable polyurethane containing lactide diol blocks capable of resorbing in vivo. The lactide diol blocks are linked with ethylene diols and/or propylene diols via urethane or urea links. By varying the proportion of ethylene diol to propylene diol, as well as the choice of the linking diisocyanate, the surface energy of the resulting polymer can be modified to achieve a desired specification. Generally, these molecules are called polyester polyurethanes or polyesters urethanes.

An example of a polyester urethane is an aliphatic polyester based poly ester urethane consisting of poly(1-lactic acid) and poly(ethylene succinate) prepared via chain-extension reaction of poly(1-lactic acid)-diol and poly(ethylene succinate)-diol using 1,6-hexamethylene diisocyanate as a chain extender. The poly(1-lactic acid)-diol is synthesized by direct polycondensation of 1-lactic acid in the presence of 1,4-butanediol. Poly(ethylene succinate)-diol can be synthesized by condensation polymerization of succinic acid with excessive ethylene glycol.

The polymer is biodegradable via hydrolysis or enzymatic cleavage. Non-polymeric materials can also be used to form the matrix and are included within the term "polymer" unless otherwise specified. Examples include organic and inorganic materials such as hydroxyapatite, calcium carbonate, buffering agents, and lactose, as well as other common excipients used in drugs, which are solidified by application of adhesive rather than solvent. In the case of polymers for use in making devices for cell attachment and growth, polymers are selected based on the ability of the polymer to elicit the appropriate biological response from cells, for example, attachment, migration, proliferation and gene expression.

An alternative material is a polyester in the polylactide/polyglycolide family. These polymers have received a great deal of attention in the drug delivery and tissue regeneration areas for a number of reasons. They have been in use for over 30 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid and poly-glycolic acid exhibit a high degree of crystallinity and degrade relatively slowly into shards. Copolymers of poly-L-lactic acid and Poly-glycolic acid are amorphous and rapidly degraded into a gel state.

The advantage of the polyester urethane polymers over the polyester polymers is that the former degrade both into a gel state and are true surface-eroding polymer. As a consequence polyester urethanes have a preferred degradation state while retaining for a longer period the original patterns of the implant. However, there are application where each are preferred.

The selection of the solvent for chemotaxic agents delivered on a resorbable polymer matrix depends on the desired mode of release of the chemotaxic agent. In the case of a totally resorbable device, a solvent is selected to deliver the chemotaxic agent alone and when delivered dissolves the deposited polymer matrix or is selected to contain a second polymer which is deposited along with the chemotaxic agent.

In the first case, the printed chemotaxic droplet locally dissolves the underlying polymer matrix and begins to evaporate and thus is adherent to the surface of the immediate underlying polymer matrix layer. In the second case, the drug is effectively deposited in the a second polymer matrix after evaporation since the dissolved polymer is deposited along with the chemotaxic agent. The first case releases the chemotaxic agent rapidly and creates the highest concentration gradient when placed in vivo. The second case releases the chemotaxic agent more slowly since release depends in part of the resorption of the carrier polymer. In this second case, the concentration of chemotaxic agent is more uniform and constant over time.

The solvent evaporation rate is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which prior layers are dissolved during application of a subsequent layer depends on the solubility of the polymer in the solvent. Fine fibers are more completely dissolved than fibers with larger diameters.

Polymer Concentration

In general, microstructural element are a resorbable polymer such as polyester urethane or polyester of molecular weight 5,000-200,000, in a solvent such as chloroform or a mixture of chloroform and a less-volatile solvent such as ethyl acetate to minimize warping. The surface energy of these can be varied by varying the proportion of hydrophilic and hydrophobic blocks in the polymer. Alternatively, a different polymer may be used such as poly-lactic acid, poly-glycolic acid or polycaprolactone.

The polymer concentration in a microstructural element solution will generally be at the limit of what can be accommodated by the nozzle, both to maximize the amount of solid polymer delivered and to minimize migration of the solvent away from the point of application in the formation of a patterned implant. Reduced solvent migration increases the resolution of the microstructural elements of prior deposited layers, e.g., reduces swelling or geometrical slumping.

The upper limit of polymer concentration is 15% for poly-L-lactic acid of 100,000 MW. This concentration of polymer may in some cases make printing of commercially viable devices impossible. The cases where the polymer is sparingly soluble, a filler may be used. Microstructural element volume can be increased by including small crosslinked or otherwise less soluble particles in the printing solution.

For example, polyglycolic acid is not soluble in chloroform or ethyl acetate. Nanoparticles of crosslinked polyester urethane can be included in the printing solution (particles up to microns in diameter can be accommodated through most nozzles) to increase the polymer content which is printed.

The amount of matter which is printed into the implant can also be increased by including small inorganic particles in the polymer solution, for example, bone derived apatite.

Manufacturing Methods

A number of processes are known for preparing microstructured molds or extrusion surfaces useful in manufacturing textured polymeric surfaces, e.g., mechanical machining, various lithography techniques, and three-dimensional printing.

Suitable manufacturing devices include both those with a continuous jet stream print head and a drop-on-demand stream print head. In the former case, a line of polymer is directed. In the second case, a drop of polymer is directed. Pointwise construction of microstructures is preferred.

A high speed printer of the continuous type, for example, is the Dijit printer made and sold by Diconix, Inc., of Dayton, Ohio, which has a line printing bar containing approximately 1,500 jets which can deliver up to 60 million droplets per second in a continuous fashion and can print at speeds up to 900 feet per minute.

Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

The object of three-dimensional printing is to create a solid state object by ink-jet printing a binder into selected areas of sequentially deposited layers of powder. In the present disclosure, this process is modified in that powder is not required. The drop or line that is initially liquid becomes a volumetric solid when deposited on a surface. In this sense, the process is more like ink in an ink-jet printing process, where a third dimension is created by the creation of successive layer of deposited polymer.

Instructions for each layer can be derived directly from a computer-aided design (CAD) representation of the patterned implant. The area to be printed is obtained by computing the area of intersection between the desired plane and the CAD representation of the object. A first layer is joined to a second layer by the liquid state of the polymer being deposited during the time of creation of the second layer. The liquid state of the second layer partially melts or dissolves into the first solid layer to form the three dimensional structure in successive layers.

While the layers become hardened or at least partially hardened as each of the layers is laid down, once the desired final implant configuration is achieved and the layering process is complete, in some applications it may be desirable that the form and its contents be heated or cured at a suitably selected temperature to further promote binding of the discrete lines or drops.

Construction of a three-dimensional component by printing can be viewed as the knitting together of structural elements, e.g., drops or lines. These elements are called microstructural primitives. The dimensions of the primitives determine the length scale over which the microstructure can be varied. Thus, the smallest region over which the surface energy of the patterned implant can be varied has dimensions near that of individual microstructural primitives. Droplet primitives have dimensions that are very similar to the width of line primitives, the difference is whether the material is laid down in a continuous line or discrete drops. The dimensions of the line primitive depend on the polymer viscosity and surface tension. A line primitive of 10 micron width is in certain cases possible, more typically the dimension is 40-60 microns. Higher print head velocities and lower polymer viscosity produce finer lines.

When solvents are used, the drying rate is an important variable in the production of patterned implants by three-dimensional printing. Very rapid drying of the solvent tends to cause warping of the printed component. Much, if not all, of the warping can be eliminated by choosing a solvent with a low vapor pressure. For example, patterned implants prepared by printing with a solution of polymer and chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

Bioactive Agents

There are essentially no limitations on the bioactive agents that can be incorporated into the patterned implants of the present invention, although those agents which produce a chemotaxic effect are most desirable in wound healing or tissue scaffolding applications. Bioactive agents need not be incorporated as a liquid, they can be processed into particles using spray drying, atomization, grinding, or other standard methodology, or those agents which can be formed into emulsifications, microparticles, liposomes, or other small particles, and which remain stable chemically and retain biological activity in a polymeric matrix, are useful.

Examples of chemotaxic agents generally include proteins and peptides, nucleic acids, polysaccharides, nucleic acids, lipids, and non-protein organic and inorganic compounds. Examples of other bioactive agents have biological effects including, but not limited to, anti-inflammatories, antimicrobials, anticancer, antivirals, hormones, antioxidants, channel blockers, and vaccines. It is also possible to incorporate materials not exerting a biological effect such as air, radiopaque materials such as barium, or other imaging agents.

In a preferred embodiment for tissue regeneration matrices, cell growth, differentiation, and/or migration modulators are incorporated into specific regions of the device at the same level of resolution as the pores and channels. These may act in combination with surface texture, surface energy, and overall shape and distribution of the microstructural elements to achieve an extracellular matrix mimic with controllable tissue directing functionality.

Of particular interest are surface-active agents which promote cell adhesion, such as an RGD peptide, or a material which inhibits cell adhesion, such as a surfactant, for example, polyethylene glycol or a Pluronic (polypropylene oxide-polyethylene oxide block copolymers).

For example, it may be desirable to incorporate adhesion peptides such as the RGD adhesion peptide into certain channels (e.g., those for blood vessel ingrowth). An adhesion peptide, such as the peptide having a hydrophobic tail marketed by Telios (La Jolla, Calif.) as Peptide, can be dissolved in water and deposited onto the surfaces of pores in the patterned implant.

The surface can be modified to prevent cellular adhesion. This may be desirable to prevent excessive soft connective tissue ingrowth into the device from the surrounding tissue, and can be accomplished, for example, by depositing an aqueous solution of a pluronic or poloxamer in the voids. The hydrophobic block of such copolymers will adsorb to the surface of the channels, with the hydrophilic block extending into the aqueous phase. Surfaces with adsorbed pluronics resist adsorption of proteins and other biological macromolecules.

In certain embodiments, the patterned implant can contain one or more of bioactive substance(s) including, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-.alpha. (TGF-.alpha.), TGF-.beta.1, TGF-.beta.2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the patterned implant can include a biologically effective amount of VEGF.

Applications Using Microstructure Implants

In certain embodiments, the patterned implant of the present disclosure can be implanted in a human subject. For example, in certain embodiments, the patterned implant of the present disclosure can be implanted in a subject by suturing the patterned implant to fat pads or muscle tissue in the lower abdomen.

In certain embodiments, the patterned implant of the present disclosure can be used to enhance vascularization in ischemic settings, such as, by acting as an angiogenic tissue scaffold to promote neovascularization and ultimately increase blood flow to regions of tissues that are not receiving sufficient blood supply. In certain embodiments, the patterned implant of the present disclosure can be implanted in a region of a subject that requires an increase in blood flow. For example, the patterned implant can be implanted in and/or near an ischemic tissue. In certain embodiments, the patterned implant can be implanted to treat cardiac ischemia. The patterned implant can be implanted to revascularize from healthy coronary circulation or neighboring non-coronary vasculature.

In certain embodiments, the patterned implant of the present disclosure can be used as a novel adjunct to coronary artery bypass grafting (CABG) in addressing cardiac ischemia. In certain embodiments, during CABG surgery, a surgeon can apply the patterned implant of the present disclosure across regions of incomplete reperfusion. For example, the patterned implant can be placed in order to revascularize from healthy coronary circulation or neighboring non-coronary vasculature (such as circulation from the left internal mammary artery) into the ischemic zone unlikely to be addressed by the CABG procedure.

In certain embodiments, the patterned implant can be used to direct neovascularization around a section of an artery subject to reduced blood flow or occlusion. In this case, the patterned implant can be used to promote revascularization of a region of ischemic myocardium in addition to a CABG procedure. In many patients that suffer from acute myocardial ischemia and in another even larger cohort of patients with untreatable coronary disease, there remain areas of viable heart that do not naturally revascularized but can be revascularized by an angiogenic tissue scaffold. In certain embodiments, the patterned implant can potentially revascularize those inaccessible ischemic zones in these patients. The selection of an alternating hydrophobic/hydrophilic arrangement of fibers of the patterned implant can stimulate and spatially direct revascularization by directing blood flow from nearby unobstructed coronary vasculature to around and beyond a coronary obstruction leading to micro-perfused distal myocardium to protect cardiomyocytes viability and function.

The patterned implant of the present disclosure can enhance neovascularization as well as influence vascular architecture through two potential mechanisms. The patterned implant can be incorporated into existing capillary beds to increase blood flow. Second, the patterned implant can deliver extracellular matrix constituents and secrete growth factors into tissue thereby providing a microenvironment that promotes angiogenesis.

The patterned implant of the present disclosure is capable of enhancing neovascularization by spatially guiding the invading sprouts of an angiogenic capillary network upon implantation, without incorporation into the nascent vessels. The patterned implant of the present disclosure can be used in conjunction with various types of engineered tissue constructs to aid in the vascularization of ischemic tissue.

In certain embodiments, the patterned implants of the present disclosure can be useful in other applications in which it would be beneficial to have an engineered material to aid in spatially guiding the direction of host cell and tissue invasion. Such applications can include, but are not limited to, nerve regeneration. In certain embodiments, the patterned implant can be seeded with a heterotypic cell suspension. For example, for nerve regeneration applications, the cell suspension can include neurons, neuronal stem cells, or cells that are associated with supporting neuronal function, or a combination thereof. In certain embodiments, the patterned implant can be used at a site of tissue damage, e.g., neuronal tissue damage.

In certain embodiments, the patterned implant of the present disclosure can allow for maintenance of the viability and proper function of a surgical repair site. For example, the patterned implant can allow for maintenance of the viability and proper function of muscle tissue surrounding a hernia repair.

In certain embodiments, the patterned implant of the present disclosure can enhance wound healing. In certain embodiments, the patterned implants can be useful in the treatment of chronic wounds such as, for example, diabetic foot ulcers. Additionally, the patterned implant of the present disclosure can be useful in the treatment of wounds sustained during military combat. In certain embodiments, the patterned implant can be implanted in a subject to treat peripheral vascular disease, diabetic wounds, and clinical ischemia.

In certain embodiments, the patterned implant of the present disclosure can be used to enhance repair of various tissues. Examples of tissues that can be treated by the patterned implant of the present disclosure includes, but is not limited to, skeletal muscle tissue, skin, fat tissue, bone, cardiac tissue, pancreatic tissue, liver tissue, lung tissue, kidney tissue, intestinal tissue, esophageal tissue, stomach tissue, nerve tissue, spinal tissue, and brain tissue.

In certain embodiments, a method of vascularizing a tissue of a subject includes providing a patterned implant comprising endothelial cells organized along lines and implanting the patterned implant into a tissue of the subject, wherein the implant promotes increased vascularity and perfusion in the subject.

To facilitate a better understanding of the present disclosure, the following examples of certain aspects of some embodiments are given. In no way should the following examples be read to limit, or define, the entire scope of the disclosure.

Example 1: Polymer

Polymers suitable for constructing patterned implants of the present disclosure are preferably absorbable in situ. Polyester Urethanes are polyurethanes copolymerized with a lactide diol.

Preparation of Lactide Diol

The raw materials:

| Compound | Source |
|---|---|
| 1,6-Hexanediol | Acros |
| Toluene | Acros |
| D,L-Lactide | SAFC |
| L,L-Lactide | Aldrich |
| Tin-ethylhexanoate | Sigma Aldrich |
| Chloroform | Sigma Aldrich |
| Diethylether | Sussmann |

This procedure is to be performed in closed vessels purged continuously with cryogenically distilled (dry) argon or nitrogen. 30 grams of 1,6-hexanediol is to be placed in 600 ml of toluene in a graduated 2 Liter flat bottom flask equipped with a magnetic stir rod. The flask is to be capped with a 2-hole stopper, one hole equipped with an input conduit and the other hole equipped with an output conduit connected to an oil trap (to prevent back flow of water vapor). The input conduit is to be connected to the nitrogen source and nitrogen flowed at approximately 5 Liters per hour. The flask is to be placed on a magnetic stirrer/hot top combination.

The toluene solution is to be stirred while raising the solution temperature to 70° C., and thereafter in 10° C. increments until the hexanediol is completely dissolved. Upon dissolution, the solution volume is to be noted. Temperature and nitrogen flow is to be continued until the solution volume drops by 150 ml. Temperature can be raised to 130° C. to facilitate toluene vaporization.

A sample of the solution is to be retrieved by syringe (to avoid contact with humid air), and the toluene removed by vacuum evaporation. A Karl Fischer water content measurement is to be performed on the solid hexanediol.

The above distillation procedure is to be continued until the water content is <300 ppm H2O by weight. The solution is to be cooled and stored under nitrogen.

Using the above setup, 150 grams of D,L-lactide and 150 grams of L,L-lactide are to be dissolved in 1750 ml of toluene by heating to 115° C., while stirring under nitrogen flow.

Upon dissolution the solution volume is to be noted and the temperature is to be raised to 130° C. The nitrogen flow is to be continued until 400 ml of toluene is removed.

A sample of the solution is to be retrieved by syringe (to avoid contact with humid air), and the toluene removed by vacuum evaporation. A Karl Fischer water content measurement is to be performed on the solid hexanediol.

The above distillation procedure is to be continued until the water content is <300 ppm H2O by weight. The solution is to be cooled and stored under nitrogen.

Weigh an appropriately sized flask (4 L). Note flask weight, preferably the weight includes closure means or the stopper with closed conduits disconnected. The hexanediol and lactide solutions are to be combined in the weighed flask, connected to nitrogen flow and stirred. The combined solution is to be heated in 10° C. increments to 70° C. After 15 minutes, 600 mg of tin ethylhexanoate is to be added drop-wise using a 1 cc syringe, while stirring vigorously. The temperature of the solution is to be raised to 120° C. in 10° C. increments. [If a temperature controlled heating mantle is used, the temperature rise will be sufficiently slow that the 10° C. heating increment can be ignored.] Turn off the nitrogen flow while keeping conduits connected such that the solution volume is closed from contact with air. While stirring and heating, react for 5 hours. Add an additional 400 mg of tin ethylhexanoate. Flush with nitrogen. Continue for an additional 3 hours. Add an additional 400 mg of tin ethylhexanoate. Flush with nitrogen. Continue for an additional 11 hours at 120° C. Reduce solution temperature to 70° C. Connect the output port of the oil trap to a vacuum source. Stop stirring and heat until toluene is removed. Discontinue vacuum. Add 800 ml of dry chloroform flush with nitrogen, stir at 70° C. until the solid is completely dissolved. The resulting turbid solution is to be filtered using a 0.2 micron PTFE filter. Remove the solvent from the filtrate under vacuum.

A sample of the dried solid is to be measured for water content using Karl-Fischer. The water content is to be <300 ppm. If not within this specification, the solid can be dried by chloroform distillation.

Preparation of Polyester Urethane
Raw Materials

| Compound | Amount of substance |
|---|---|
| IPDI (Isophorone diisocyanate) | 202.9 mmol |
| 1,4-Butanediol | 142.8 mmol |
| Toluene | 2000 mL |
| Dibutyltin dilaurate | 11.6 mmol |
| PTMG 2000 (Terathane 2000) | 20.1 mmol |
| PLA Diol AP1756 | 40.3 mmol |

All operations are to be performed under nitrogen and dry solvents.
Suggested Equipment:

A 2 Liter, four-port graduated glass reactor with central port for introduction of motor propelled stir rod is recommended. The stir rod is preferably multi-tier with angled blades to avoid laminar mixing. The reactor is to be equipped with a heating mantle fitted with a thermocouple and a programmable temperature controller. [Preferably, the mantle has cooling capability as well, in which a fluid filled mantle is used in conjunction with a circulating control unit.] Preferably the reaction volume is not exposed to the thermocouple, but rather the thermocouple is embedded in the heating mantle. Due to the high viscosity of the final product and need for rapid and complete mixing, use of a magnetic stir rod is discouraged. The two free ports are to be equipped with conduits for delivery and removal of nitrogen. The output port is to be connected to an oil trap to prevent backflow of water vapor. Ideally the conduits contain valves to provide for transport of the reaction volume without exposure to air. The last port, the diagnostic port, is to be used for addition and retrieval of reaction volume. The nitrogen atmosphere should be delivered at positive partial pressure to compensate for the external stirring means and periodic opening of the diagnostic port. The partial pressure is indicated by the observation of nitrogen bubbles in the oil trap, and the rate of their creation can be used to set and maintain a reasonable nitrogen flow rate.

Purge the reactor with nitrogen. Add 40.32 grams of PLA diol, obtained from the procedure above and 40.11 grams of Terathane 2000 and 810 ml of toluene using the above setup. Set the stir rate to 100 cycles per minute. The dissolution is accomplished by heating to 115° C., while stirring under nitrogen flow.

Upon dissolution the solution volume is to be noted and the temperature is to be raised to 130° C. The nitrogen flow is to be continued until 200 ml of toluene is removed. Cool the reactor to 15° C. (or room temperature, if the mantle is not equipped with coolant). While stirring, add via the diagnostic port and under nitrogen flow, 30 ml toluene followed by 45.09 grams of IPDI. Stir for 30 minutes. Add drop wise, 6.74 ml dibutyltin dilaurate.

Using the diagnostic port, remove a sample of the solution to measure the % NCO. The % NCO can be measured using dibutylamine back titration. By this method, it is traditional to take at least 3 NCO measurements, or you may do so until a desired standard deviation is obtained. Raise the temperature of the reactor to 75° C. React the mixture under nitrogen flow for 4 hours at 75° C. Take an NCO. React for another 1 hour, take an NCO. If the NCO at 5 hours is less than 95% of the measurement at 4 hours, continue to react for 1 hour durations until the NCO change is less than 5% between consecutive measurements. Using the setup of the preparation of the PLA diol, dissolve 12.872 g of butanediol in 230 ml of dry toluene. Dissolution is accomplished by heating to 75° C. Add the butanediol solution to the reactor. React the mixture under nitrogen flow for 9 hours at 75° C. Take an NCO. React for another 1 hour, take an NCO. If the NCO at 10 hours is less than 95% of the measurement at 9 hours, continue to react for 1 hour durations until the NCO change is less than 5% between consecutive measurements. During the course of this procedure, toluene may be added to reduce the viscosity of the reactant and improve mixing. Considerable torque can develop during this reaction. When the NCO has stabilized [this should be reproducible from batch to batch, if not water is entering the system], decant the reaction volume to a vacuum chamber. This is easier performed if the reaction volume is still hot. Apply vacuum and remove the toluene, and the resulting solid is to be dissolved in 1000 ml THF. The polymer is the precipitated in 15 L of pentane, filtered and repeated washed with pentane and dried under vacuum at 50° C. n-Pentane can be obtained from Acros and was used after redistillation and THF (also from Acros) was used as received. The resulting polyester urethane has a melt temperature of 132° C. and is soluble in most solvents, for example toluene and acetone.

Example 2: Bioactive

All of the synthesis that is detailed below are to be performed in a hermetically sealed glass reactor equipped with a stir rod and temperature controlled jacket. The headspace of the reactor is to be continuously flushed with dry nitrogen unless otherwise specified.

Example 2a: Preparation of a Polyester Diisocyanate

In this example a castor-derived hydroxyl-terminated ricinoleate derivative is used as the diol. One equivalent of polycin D-265 (212 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (424 Dalton+2×174 Dalton) yielding approximately 10.9%.

Alternatively, a lower molecular weight diol may be used, such as polycin D-290 where 1 equivalent of polycin D-290 is 193 g and the target % NCO is 84/(386+348)=11.4%.

Alternatively, a higher molecular weight diol may be used, such as polycin D-140 where 1 equivalent of polycin D-140 is 400 g and the target % NCO is 84/(800+348)=7.3%.

All polycin diols are available from Performance Materials (Greensboro, N.C.) and toluene diisocyanate is available from Sigma-Aldrich (Milwaukee, Wis.).

Example 2b: Preparation of a Polyether Diisocyanate

In this example a polyether hydroxyl-terminated copolymer of 75% ethylene oxide and 35% propylene oxide is used as the diol. One equivalent of UCON 75-H-450 (490 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (980 Dalton+2×174 Dalton) yielding approximately 6.3%. Polyether copolymers of ethylene oxide and propylene oxide diols are available from Dow Chemical (Midland, Mich.).

Example 2c: Preparation of a Polyester Triisocyanate

In this example a castor-derived hydroxyl-terminated ricinoleate derivative is used as the triol. One equivalent of polycin T-400 (141 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=13.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (282 Dalton+2×174 Dalton) yielding approximately 13.3%.

The above reaction will yield a viscous product. A less viscous product can be obtained by adding propylene carbonate to the initial mixture. Additions up to 100% by weight of propylene carbonate are useful. Adjustment to the target NCO of the mixture must be performed using standard methods, or the propylene carbonate may be added after reaching the target % NCO. Propylene carbonate is available from Sigma-Aldrich (Milwaukee, Wis.).

Example 2d: Preparation of a Polyether Triisocyanate

In this example a polyether hydroxyl-terminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Example 2e: Preparation of a Polyol Triisocyanate from Polyol Diol

Any of the diisocyanates prepared in Examples 2a and 2b can be trimerized by the addition of a low molecular weight triol such as polycin T-400 or trimethylolpropane (TMP). In this example TMP is used, but the method is adaptable to any triol. Complete trimerization of the diisocyanates of Example 2a and 2b will result in viscous products. To yield a lower viscosity product propylene carbonate can be employed or less triol can be used. In the later case, a mixture of diisocyanate and triisocyanate is obtained.

In this example the product of Example 2b is used as the polyether diisocyanate. One equivalent of Example 2b (682 g) is combined with 0.1 equivalent TMP (44.7 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=5.8%. The target % NCO is reached when every hydroxyl group in the mixture is reacted with an NCO group. The ideal % NCO is calculated by dividing the weight fraction of the functional isocyanate groups 10%(3×42 Dalton) and 90%(2×42) per product molecule by the total weight fraction of the product molecule (3×1364 Dalton+134 Dalton)+1364 yielding approximately 0.3%+5.5%=5.8%.

TMP is available from Sigma-Aldrich (Milwaukee, Wis.).

Example 2f: Preparation of a Modified Boswellia Extract Using the Triisocyanate of Example 2d The hydroxyl number of Boswellia extract will vary depending on extraction method, species of Boswellia extracted, and even variations within species. The goal is to obtain a product with no NCO functionality, so all reaction mixtures should be reacted until the final % NCO=0.

In this example the product of Example 2d is used as the polyether triisocyanate mixture. One hundred grams of Example 4 is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 then an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained.

Example 2g: Preparation of a Modified Boswellia Extract Using the Triisocyanate/Diisocyanate of Example 2e The hydroxyl number of Boswellia extract will vary depending on extraction method, species of Boswellia extracted, and even variations within species. The goal is to obtain a product with no NCO functionality, so all reaction mixtures should be reacted until the final % NCO=0.

In this example the product of Example 2e is used as the polyether diisocyanate/triisocyanate mixture. One hundred grams of Example 2e is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 then an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained.

Example 2h: Preparation of a Highly-Branched Modified Boswellia Extract with Absorbable Links Diol and triol can be combined to form a multi-branch polymer. In this instance, the Multranol 9199 triol is chain extended with polycin D-265 diol. The diisocyanate form of Example 2 is useful in chain extending the triisocyanate form of Example 4. We wish to have on average 2 diisocyanates for every 3 triisocyanates, which forms a 5 armed isocyanate.

In this example 0.09 equivalents (292 g) of Example 2d is mixed with 0.04 equivalents (26.6 g) of Example 2b. The triisocyanates of Example 2d and diisocyanates of Example 2b are chain extended with 0.08 equivalents lysine diamine to form a 5 armed isocyanate. One hundred grams of this reaction product is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 then an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained. Lysine diamine is available from Sigma-Aldrich (Milwaukee, Wis.).

Thus, although there have been described particular embodiments of the present invention of a new and useful Device with Microstructure Mediated Absorption Profile it is not intended that such references be construed as limitations upon the scope of this invention except as set forth in the following claims.

What is claimed is:

1. An absorbable polymer medical device comprising an implant, the implant including a microstructured surface having at least one morphological feature with a dimension ranging from 5 to 200 microns, wherein the implant comprises a polymer that is degradable in vivo by hydrolysis or enzymatic degradation, and wherein upon degradation, the implant develops a polymer skin, but said polymer skin is no greater than 100% of the at least one morphological feature dimension.

2. The device of claim 1, wherein the microstructured surface comprises at least two morphological features, wherein the first morphological feature comprises i) a height of 5 to 50 microns and ii) a width of 5 to 50 microns, the second morphological feature comprises i) a height of 50 to 200 microns and ii) a width of 50 to 200 microns, and further wherein the first morphological feature is disposed on the surface of said second morphological feature.

3. The device of claim 1, wherein the implant is a sheet having a flexural modulus, and the flexural modulus of the implant is less than a flexural modulus of a sheet of the polymer that does not comprise the microstructured surface, where the sheets have the same thickness.

4. The device of claim 3, wherein a force required to puncture the implant with a surgical suture is less than the force required to puncture the sheet that does not comprise the microstructured surface.

5. The device of claim 3, wherein the implant requires a shear force of translation greater than a sheet that does not comprise the microstructured surface when implanted in a mammalian body.

6. The device of claim 1, wherein the microstructured surface promotes cellular infiltration.

7. The device of claim 1, wherein the implant degrades into solid fragments having a size smaller than the largest morphological feature of the microstructured surface after implantation into a mammalian body.

8. The device of claim 1, wherein the implant does not degrade into solid fragments or particulates after implantation into a mammalian body.

9. The device of claim 1, the implant further comprising first and second sides, wherein the first side comprises the microstructured surface and the second side does not.

10. The device of claim 1, the implant further comprising first and second sides, wherein the first side comprises the microstructured surface and the second side comprises a second microstructured surface.

11. The device of claim 1, wherein the implant is adhered to a surgical mesh.

12. The device of claim 1, wherein the polymer is selected from the group consisting of polymers of lactide, glycolide, caprolactone, dioxanone, trimethylene carbonate, orthoesters, ethylene oxide, propylene oxide, urethane and combinations thereof.

13. The device of claim 1, wherein the polymer is a polyester polyurethane.

14. The device of claim 13, wherein the polyurethane is a copolymer comprising polylactide, a polyester selected from the group consisting of polyethylene oxide; polypropylene oxide; tetrathane; and mixtures thereof.

15. The device of claim 1, wherein the implant further comprises an elastomeric, bioabsorbable core portion having an outer surface comprising the microstructured surface, the microstructured surface comprising a plurality of discrete hierarchically arranged morphological features arranged periodically such that an exposed portion of the morphological features project outwardly from the outer surface, the exposed portion of said microstructures and said outer surface of said core portion in combination providing an outer surface of said implant, wherein the outer surface of said implant has a self-similar topography comprising at least two microstructured scales such that upon implantation the exposed portion of the plurality of morphological features project outwardly from said outer surface of said core portion; and after the morphological features are absorbed, the outer surface of the core portion has a soft partially dissolved skinless layer thereon.

16. The device of claim 15, wherein said elastomeric core portion comprises polylactic acid, polyglycolic acid, or a combination of polylactic acid and polyglycolic acid.

17. The device of claim 16, wherein said elastomeric core portion comprises a polyester polyurethane.

18. The device of claim 1, wherein the implant has at least one preferential hydration zone associated with a first portion of the surface of said implant adapted to hydrate within the environment more quickly than a second portion of the implant, the hydration zone comprising a microtextured surface that modifies the surface energy of the polymer.

19. The absorbable device of claim 1, wherein the implant comprises a sheet comprising the polymer, the sheet having at least one first portion of morphological features disposed on a second portion of morphological features, wherein said first portion has a spatial periodicity ranging from about 100 to about 500 microns between morphological feature centers, the second portion has a spatial periodicity ranging from about 100 to 10 microns between morphological feature centers, the sheet ranging in thickness from about 10 microns to about 2,000 microns, and, upon absorption of a fluid, the second morphological features expand geometrically and have a volume expansion ranging from about 10% to about 100%, and, in the expanded state, have a density ranging from about 0.1 g/cm3 to about 1.5 g/cm3.

* * * * *